(12) United States Patent
Segal et al.

(10) Patent No.: US 9,982,216 B2
(45) Date of Patent: May 29, 2018

(54) POLYHYDROXYLATED FATTY ALCOHOLS

(71) Applicant: POLYOL BIOTECH LTD, Caesarea (IL)

(72) Inventors: Joseph Segal, Haifa (IL); Gennady Rosenblat, Haifa (IL)

(73) Assignee: AVOMED Ltd., Rosh Pina (IL)

( * ) Notice: Subject to any disclaimer, the term of this patent is extended or adjusted under 35 U.S.C. 154(b) by 477 days.

(21) Appl. No.: 14/414,215

(22) PCT Filed: Jul. 10, 2013

(86) PCT No.: PCT/IL2013/050591
§ 371 (c)(1),
(2) Date: Jan. 12, 2015

(87) PCT Pub. No.: WO2014/009957
PCT Pub. Date: Jan. 16, 2014

(65) Prior Publication Data
US 2015/0175933 A1      Jun. 25, 2015

Related U.S. Application Data

(60) Provisional application No. 61/669,685, filed on Jul. 10, 2012.

(51) Int. Cl.
| | | |
|---|---|---|
| *C11B 1/10* | (2006.01) |
| *A61Q 19/00* | (2006.01) |
| *A61K 31/047* | (2006.01) |
| *A61K 36/54* | (2006.01) |
| *C11B 11/00* | (2006.01) |
| *A61K 8/92* | (2006.01) |
| *A61K 8/34* | (2006.01) |
| *A61K 8/37* | (2006.01) |
| *A61K 8/97* | (2017.01) |
| *A61K 31/231* | (2006.01) |

(52) U.S. Cl.
CPC .............. *C11B 1/10* (2013.01); *A61K 8/345* (2013.01); *A61K 8/375* (2013.01); *A61K 8/922* (2013.01); *A61K 8/97* (2013.01); *A61K 31/047* (2013.01); *A61K 31/231* (2013.01); *A61K 36/54* (2013.01); *A61Q 19/00* (2013.01); *C11B 11/00* (2013.01); *A61K 2236/33* (2013.01)

(58) Field of Classification Search
None
See application file for complete search history.

(56) References Cited

U.S. PATENT DOCUMENTS

| | | | |
|---|---|---|---|
| 6,582,688 B1 | 6/2003 | Broutin et al. | |
| 2011/0217251 A1* | 9/2011 | Meretzki | A61K 31/047 424/59 |
| 2011/0250154 A1 | 10/2011 | Meretzki et al. | |
| 2013/0216488 A1 | 8/2013 | Hernandez-Brenes et al. | |

FOREIGN PATENT DOCUMENTS

| | | |
|---|---|---|
| WO | WO2010026595 | 3/2010 |
| WO | WO2010026596 | 3/2010 |
| WO | WO2012042404 | 4/2012 |

OTHER PUBLICATIONS

Dabas (Journal of Food Science (Nov.-Dec. 2011), vol. 76, No. 9, pp. C1335-41).*
Rosenblat G et al: "polyhyroxylated fatty alcohols derived from avocado suppress inflammatory response and provide non-sunscreen protection against UV-induced damage in skin cells" Archives of Dermatological Research 2011 Springer Verlag DEU, vol. 303, No. 4, May 2011, pp. 239-246, XP55025943, ISSN: 0340-3696.
Nagraj M: Antioxidant and antibacterial activity of avocado (Persea gratissima Gaertner.) seed extract. World Applied Aciences Journal, vol. 9 No. 6, Jan. 1, 2010, p. 695 XP009187804.
Maria Ramos-Jerz: "Phytochemical analysis of avocado seeds (Persea Americana Mill.,c.c. Hass)" In: Phytochemical analysis of avocado seeds (Persea Americana Mill.,c.c. Hass), Jan. 1, 2007, Gottingen Cuvillier: Gottingen, DE, XP055163494.
Imafidon, K.E, Igbinaduwa P. The Effect of Aqueous Extract of P. Americana Mill. (Avocado) Seeds on Blood Pressures and Electrolytes in Hypertensive Rats.Biosci Biotechnol Res Asia 2010;7(1).
International Search Report for PCT application No. PCT/IL2013/050591 dated Oct. 22, 2013.
Supplementary European Search Report for EP patent application No. 13817501.3 dated Jan. 11, 2016.

* cited by examiner

*Primary Examiner* — Susan Hoffman
(74) *Attorney, Agent, or Firm* — Pearl Cohen Zedek Latzer Baratz LLP

(57) ABSTRACT

A process of obtaining avocado seed extracts comprising polyhydroxylated fatty alcohols (PFAs), the process comprising crushing raw undried avocado seeds; incubating the crushed avocado seeds; and extracting PFAs from the crushed seeds with an organic solvent.

11 Claims, 4 Drawing Sheets

POLYHYDROXYLATED FATTY ALCOHOLS

FIELD OF THE INVENTION

The present invention relates to fatty alcohols. More particularly, the present invention relates to acetylated and unacetylated polyhydroxylated fatty alcohols.

BACKGROUND OF THE INVENTION

Avocado fruits are widely consumed as food throughout the world, and are also diversely used for medicinal and cosmetic purposes. Various preparations containing freshly mashed avocado as well as avocado oil are recommended to be applied onto the skin to revitalize and to improve its appearance.

Many studies have been conducted regarding non-saponifiable fractions of avocado oil. The unsaponified material (non-saponifiable fraction) is the fraction of fatty material that is insoluble in water and may be extracted with an organic solvent after a prolonged alkaline hydrolysis. Oil saponification is used for isolating free fatty acids from triglycerides that compose more than 90% of plant-origin oil. To a certain extent, unsaponifiables are the byproducts of soap technology although the presence of some unique phytochemicals makes unsaponifiables useful ingredients for cosmetic and pharmaceutical applications in their own right. The content of non-saponifiables in avocado oil ranges from 2% to 7%, and they are a very attractive fraction of avocado extracts for cosmetic and therapeutic applications, due to the biological activity of their constituencies.

Polyhydroxylated fatty alcohols (PFA) are unique crystalline lipid molecules that may be found in avocado extracts. PFA lipids all have a long aliphatic (mostly C17) chain with one end unsaturated with a double or triple (acetylenic) bond, and the other end having three hydroxyl groups. Naturally, one of the hydroxyl groups in position 1 or 4 of most PFAs are acetylated, as shown in structures A, B, D, E In FIG. 1. Studies of biological activity of PFA demonstrated antifungal [Dominguez, F et al., 2005, Phytochemistry 54, 183-189], antibacterial [Neeman, I. et al., 1970, Appl. Microbiol. 19, 470-473] and anti-parasitic properties [Abe, F., et al., 2005. Biol. Pharm. Bull. 28, 1314-1317] and show to inhibit acetyl CoA carboxylase activity [Hashimura H, et al., (2001) Biosci Biotechnol Biochem 65:1656-1658].

A recent study demonstrated the photo protective and anti-inflammatory potential of PFAs at the molecular level [Rosenblat G et al., Arch Dermatol Res. 2011 May; 303(4): 239-46].

In separate experiments, it was demonstrated that polyhydroxylated fatty alcohols attenuate experimental dermatitis and may be used topically in pharmaceutical applications [Otuki, M. F., et al., 2011, Eur. J. Pharmacol. 672,175-179].

From a practical point of view, avocado oil unsaponifiables comprising non-acetylated PFA in a mixture with other extracted materials are useful in cosmetic and medicine.

Non acetylated fatty alcohols (such as structures C and F in FIG. 1) are naturally present in avocado seeds in minor amounts compared to the levels of the acetylated fatty alcohols. However, during saponification, the acetyl groups are essentially separated from the non-acetylated polyhydroxylated fatty alcohols. Thus, avocado oil non-saponifiables contains mostly acetyl-free PFA, which determine many of the biological properties of avocado unsaponifiables.

The known technique for obtaining unsaponifiables (as a part of the technological process for oil isolation and soap production) is extraction of avocado oil followed by alkaline saponification with potassium hydroxide or sodium hydroxide in alcoholic medium. The hydrolyzed compounds are extracted with a suitable organic solvent, for example petroleum ether, ethyl ether or any other suitable solvent that is immiscible with the aqueous-alcoholic solution. After several stages of washing and solvent evaporation, the extract of unsaponifiable may be used for formulations or may be additionally fractionated by different methods.

For example, U.S. Pat. No. 6,582,688 describes the use of molecular distillation for obtaining fractions of avocado unsaponifiables obtained from fruit pulp. The distillate is enriched with furan lipids or mixtures of furan lipids and polyhydroxylated fatty alcohols. In general, the material from avocado is obtained by controlled drying of the fruit pulp, extraction of the crude oil by cold pressing, preliminary molecular distillation of the oil, saponification of the distillate with ethanolic potassium hydroxide, extraction of the unsaponifiable material in a countercurrent column with an organic solvent, filtration, washing, desolation and deodorization. The material from the avocado fruits obtained by the above described method is then resubjected to the step of molecular distillation.

Such methods are lengthy and labor intensive. An object is to provide easier methods of producing acetyl-free PFAs.

SUMMARY OF THE INVENTION

According to one aspect, a process of obtaining avocado seed extracts comprising polyhydroxylated fatty alcohols (PFAs), is provided, the process comprising:
crushing raw undried avocado seeds;
incubating the crushed avocado seeds;
extracting PFAs from the crushed seeds with an organic solvent.

Preferably the organic solvent is selected from methanol and alkyl acetates.

Most preferably, the solvent is butyl acetate.

Preferably, the incubating is at room temperature.

The process should not require saponification of the crushed seeds.

The incubating is usually complete within about 48 hours.

The incubating may be allowed to continue until acetylated PFAs in the crushed avocado seeds are endogenously de-acetylated to a predicted degree.

Preferably the crushed seeds are provided at a bulk density between about 0.2 and 1.2 g/ml.

Most conveniently, the crushed seeds are at a bulk density between about 0.6 and 0.8 g/ml.

The incubating is typically carried out at a temperature between 15 and 45° C.

Preferably, 1 to 6 parts of the solvent are used per about 1 part of the crushed seeds.

More preferably, about 3 parts of the solvent are used per about 2 part of the crushed seeds.

In some embodiments, the extracting comprises mixing the crushed seeds for about 1-5 hours with the solvent.

Usually the mixing is for about 2 hours.

The process may further comprise filtering the extract.

In preferred embodiments, the production further comprises evaporating solvent from the extract by distillation.

In some embodiments, the method further comprises subsequently dissolving the extract in hot hexane.

Typically, cool precipitation of PFAs out of the hexane solution is then subsequently performed.

The method should exclude lyophilisation of the crushed seeds.

According to another aspect, an extract of raw and undried crushed avocado seeds, comprising a substantial amount of PFAs is provided.

The extract typically further comprises trace amounts of a extracting solvent, wherein the extracting solvent is butyl acetate.

The extract is typically essentially furan-lipid free.

A cosmetic composition comprising PFAs may be prepared from the extract.

A therapeutic composition comprising PFAs may be prepared from the extract after redissolving the crude extract in hexane and performing cool precipitation.

The precipitate is essentially furan-lipid free.

According to another aspect, use of deacetylated PFAs for the manufacture of a medicament for amelioration of skin damage is provided, wherein the medicament comprises a major amount of deacetylated PFAs and a minor amount of acetylated PFAs.

According to another aspect, use of acetylated PFAs for the manufacture of a medicament for the protection of skin is provided, wherein the medicament comprises a major amount of acetylated PFAs and a minor amount of deacetylated PFAs.

Unless otherwise defined, all technical and scientific terms used herein have the same meaning as commonly understood by one of ordinary skill in the art to which this invention belongs. Although methods and materials similar or equivalent to those described herein can be used in the practice or testing of the embodiments, suitable methods and materials are described below, in case of conflict, the specification, including definitions, will control. In addition, the materials, methods, and examples are illustrative only and not intended to be limiting.

BRIEF DESCRIPTION OF THE FIGURES

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention, hi this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION

Figure 1:
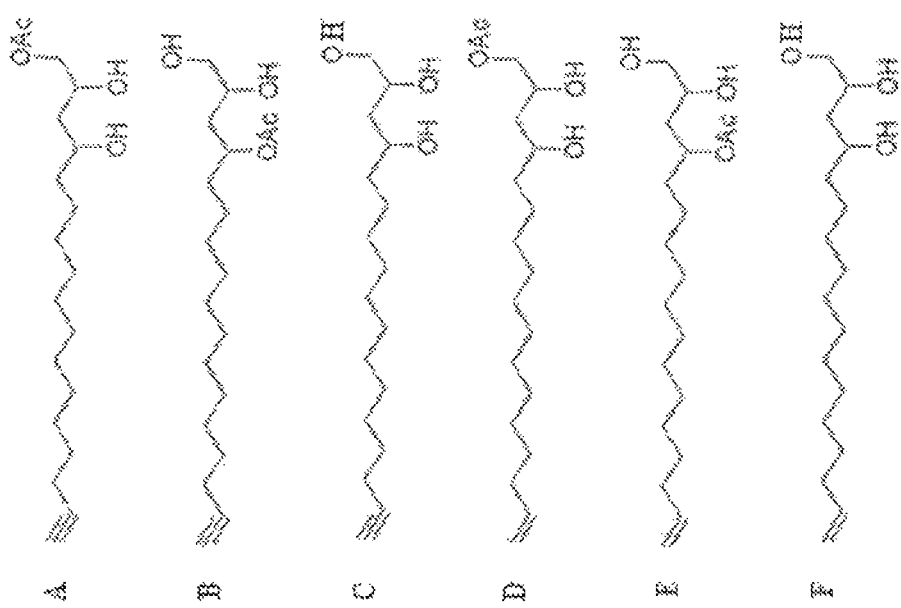
FIG. 1 shows several forms of polyhydroxylated fatty alcohols naturally present in avocado.

It has now surprisingly been found that acetyl-free PFA may be obtained in the form of extracts without resorting to alkaline hydrolysis and molecular distillation processing, using untreated avocado seeds as a source of PFAs. Avocado seeds are an important source for avocado non-saponifiables, although the seeds are often considered technological waste since the extracts are very bitter. The avocado seed compounds, extracted by organic solvent, include PFA, triglycerides, furanic lipids, and other minor compounds, such as tocopherols, sterols, pigments etc.

Surprisingly, in crushed raw avocado seeds that had not been subjected to any treatment (such as drying at elevated temperatures or lyophilisation), and that were stored (incubated) after crushing at room temperature for 48 h, almost all polyhydroxylated fatty alcohols were detected in the form of de-acetylated compounds. This phenomenon may be due to release and activation of endogenous enzymes in crushed avocado seeds, which catalyse deacetylation of polyhydroxylated fatty alcohols. The de-acetylation process is time dependent. One hour after crushing up to 15% of the polyhydroxylated fatty alcohols are deacetylated. After 24 h, the levels of deacetylated (acetyl free) PFAs range from 40%-70% of the total PFAs. Almost all de-acetylation is achieved by 48 h after crushing. Subsequently the PFA may be extracted from crushed avocado seeds by extraction with suitable solvents (preferably butyl acetate) for 1-5 hours, followed by solvent evaporation.

Thus, a new technological extraction process for obtaining avocado seed extracts containing acetyl free PFA comprises the following steps:
1). crushing intact avocado seeds;
2). incubating the crushed raw material for at least 24 hours, optionally up to about 48 hours, preferably at a temperature range of 15-45° C., most preferably 18-30°;
3). extracting fatty acids from the crushed material with an organic solvent (preferably, butyl acetate);
4). evaporating the solvent;
5). optionally isolating substantially pure acetyl-free PFA by dissolving the extract in hexane, and
6) cool precipitation of PFA at a temperature of about 2-8° C. for about 15-24 hours. The last two stages are preferable, but not a necessity, since the crude extract (from evaporation of butyl acetate) may be used as is for cosmetic applications.

A number of technologically and environmentally safe and suitable (for cosmetic, medicinal and nutritional applications) solvents were tested for PFA extraction including ethanol isopropanol, propylene glycol ethyl acetate, and butyl acetate. The reasons butyl acetate were chosen were numerous: for example,—lower flash-point compared to ethyl acetate make butyl acetate the safer solvent. From this point of view butyl acetate is an ideal solvent. Furthermore, ethanol, iso-propanol and propylene glycol—were discovered to be unsuitable because PFAs are found to decompose during the extraction procedures in these solvents. We suggest that PFA decomposition is associated with the acidic properties of alcoholic compounds, and coincidental catalytic activity of some extracted compounds. Surprisingly, such decomposition did not seem to occur in butyl acetate. Comparing the solvents ethyl acetate and butyl acetate, ethyl acetate extracts generally appeared to be more "dirty", imparting gray color to the extract etc.

After evaporation of butyl acetate, the dried extract typically contains trace amounts of butyl acetate, typically 0.01% to 0.03% of the extract weight, as measured in gas chromatography. The solvent may be further removed by applying a higher sub-pressure during the evaporation of the solvent, however such effort is merely wasteful and the trace butyl acetate is harmless.

The crude extract (also known as oleo resin) typically comprises about 40% TFAs, as well as further comprising triglycerides, phytosines and traces of furan lipids, the latter qualitatively determined from very small spots appearing in TLC of the crude extracts.

The dissolution of the extract in hexane essentially leaves behind the trace amounts of undissolved furan lipids, and the content of PFAs in the crystallized product is typically over 90%, more typically 95% or more. The crystallized product may be suitable for medical applications.

Following is a comparison of technological processes for isolation of PFA-containing extracts by commercially available methods (isolation from avocado fruit pulp) and the present method (isolation from avocado seeds). The comparison is demonstrated in table 1.

TABLE 1

| From avocado fruit pulp according to U.S. Pat. No. 6,582,688 | From avocado seeds, according to present method |
| --- | --- |
| 1. Fruit drying (up to 48 h, 80° C.-120° C.) | Avocado seed crushing |
| 2. Oil extraction | Incubation at room temperature (15° C.-45° C.), up to 48 h |
| 3. Preliminary molecular distillation of triglycerides (180° C.-230° C.; $10^{-3}$-$10^{-2}$ mmHg) | Extraction with an organic solvent, e.g. butyl acetate (1-5 h; 15° C.-45° C.) |
| 4. Alkaline hydrolysis (saponification, 12N potassium hydroxide in ethanol, refluxed for 4 h) | Butyl acetate evaporation (40° C.-50° C.), vacuum = (Extract is ready to be used) |
| 5. Extraction of unsaponifiables with organic solvent, repeated 5-6 times | Optional isolation of PFA by cool precipitation from hexane (hot hexane- 40° C.-50° C./ 15 min; 4° C.-8° C., 15-24 h) PFA concentration in final extract is up to 95% |
| 6. Solvent evaporation (Extract is ready to be used) | |
| 7. Final processing (molecular distillation, deodorization etc) PFA concentration described* fo one of the final distillate fractions - 25.5% | |

The optimal ratio of crushed seeds to butyl acetate is about 1:3 respectively.

The ratio of crude extract to hexane may be between 1:1 to 1:6, respectively, preferably about 2:3.

One advantage of the method described below may be that the acetyl-free fatty alcohol—containing seed extracts may be obtained while avoiding the stage of alkaline hydrolysis.

Another advantage may be reducing energy expenditure by obviating the heating of the source material.

Another advantage may be obtaining the extracts essentially free of furan lipids (at concentrations in the extract substantially lower than the levels of the acetyl-free alcohol), in contradistinction to the method of U.S. Pat. No. 6,582,688, where the preliminary seed (or row material) drying and temperature promote cyclization of the furan lipid precursors. As said above, the presence of furan lipids is barely detectable in crude extracts. After cool precipitation, the crystals may be redissolved in hexane and samples run in silica TLC, no furan lipid spots were observed on the plates.

Moreover, an advantage of this technology is that it may be used for obtaining avocado seed extracts comprising mixtures of acetylated and acetyl-free fatty alcohols in various relative amounts. This control of relative amounts may surprisingly be achieved by reducing the period of incubation of crushed avocado seeds prior to extraction, resulting in partial hydrolysis of acetyl groups of PFA molecules. A reason for using mixtures of both compounds is that the biological properties of the acetylated and acetyl-free PFA are different and sometimes complimentary.

Comparative studies revealed the difference in antibacterial activity between acetylated and de-acetylated fatty alcohols. It has also been demonstrated that de-acetylated PFA (obtained by alkaline hydrolysis of acetylated PFA) in vitro had an enhanced effect of inhibiting hydrolysis of phospholipids by bee venom PLA2, i.e. having the same inhibiting effect at a 10 fold less concentration level than acetylated PFA.

In another study, hydrolysis of acetyl groups significantly increased the cytotoxic and inhibiting effect of PFA on T-cells proliferation These paradigms clearly demonstrate the contribution of acetyl groups to the biological activity of the molecules.

These observations allowed us to extend the application of PFA and PFA-containing extracts by using both acetylated and acetyl-free PFA mixtures, and the compounds separately, depending on the application. This statement may be clearly explained by the example already mentioned above concerning the effect of PFA on T-cell proliferation.

It is commonly accepted that T-cell proliferation and infiltration of inflammatory induced-cells to the damaged tissue are the major activators of the inflammatory process. Inhibition of T-cell proliferation and/or activity may be considered as useful to delay this process. Currently, a number of T-cell inhibitors are known as useful for the treatment of various pathogenic conditions. In this context, we have discovered that the application of acetyl free-PFA demonstrates stronger inhibition of T-cells, and is thus preferable.

On the other hand, we have discovered an ameliorative and photo-protective (but not sun-screening) effect of PFA in acute UVB-induced skin damage which is not associated with anti-T cell proliferative activity of PFA. Among many deleterious effects, UV-B is known to have an immune-suppressive effect, including inducing loss of contact hypersensitivity and of immune tolerance. In this context, additional inhibition of already inhibited T-cells by acetyl-free PFA in applications to UV-B-damaged skin may significantly decrease the benefits of using deacetylated PFA for amelioration of photo-damaged skin. In this case, application of acetylated PFA for skin photoprotection is found to be preferable. In contrast, application of deacetylated PFA is found to be more desirable in case of inflammatory conditions for strong inhibition of T-cell proliferation and cytokine expression. Thus in some cases using some more acetylated PFA and less deacetylated PFA in skin applications—may be desired, and in other cases the reverse applies.

It was thus not formerly realized, and has now been found, that cosmetics and medicaments comprising major levels of deacetlyated PFAs and minor levels of acetylated PFAs should be used for amelioration of skin, whereas cosmetics and medicaments comprising major levels of acetylated PFAs and minor levels of deacetylated PFAs should be used for skin protection from UV-B radiation and/or air pollution.

The ameliorative medicament may be manufactured from crushed seeds that were incubated for example for 48 hours, whereas the prophylactic may be manufactured from crushed seeds that underwent a much shorter, if any, incubation.

Another advantage of this method is that the final extracts may contain substantial amounts of both—acetylated and acetyl free PFA and avocado seed triglycerides (in concentrations up to 30% of the dried extract) by commencing the extraction before essential completion of the conversion of the acetylated PFA to deacetylated PFAs, and may comprise unique combinations of unsaturated fatty acids that are not present in extracts obtained from the material after alkaline hydrolysis.

Furthermore, in currently used methods involving alkaline saponification, the triglycerides undergo hydrolysis by the basic conditions, and the resulting extract of unsaponofiables thus does not contains triglycerides, which in avocadoare beneficial, being extremely rich in monounsaturated oleic acid, and also contain a balanced proportion of omega-3 and omega-6 fatty acids).

It is further notable that the present method is simpler and more cost effective that our method described in

EXAMPLES

Example 1

Determination of PFA Transformation Products in Intact and in Crushed Avocado Seeds Seeds were separated from Ettinger avocado pear sand were crushed to bulk density range of 0.6-0.8 g/ml. A first portion of 400 g was immediately extracted with 600 ml butyl acetate for two hours under intensive mixing. A second similar portion of crushed avocado seeds was stored for 48 hours in a sealed plastic cup at room temperature prior to the extraction process. After finishing the extraction stage, butyl acetate was evaporated from all samples and the concentration of PFA in dried extracts was determined by GC.

In addition, extracts were re-dissolved in hot hexane, and then were put in a cooling room at a temperature between 5-8 C.° for 15-18 hours for cool crystallization. The crystallized products (mainly consisting of PFA) were also analyzed by GC-analysis.
Results Acetylated PFAs typically have retention times around 5.05 min, 4.88 min, 4.81 min and 4.66 min on a GC column. Two main peaks with retention times of 5.05 and 4.81 were used for acetylated PFA quantification.

Crushing avocado seeds caused an apparent decrease in acetylated PFA concentration during the incubation of the crushed seeds. Moreover, reduction in acetylated PFA concentration correlated with the apparent formation of two other compounds with retention times around 4.2 and 4.0 min on the same GC capillary column. These compounds co-precipitated with acetylated PFA in the cool precipitation process, and their corresponding peaks on GC chromatogram are usually present in minor amounts. Acetylated PFA concentration in the samples that were incubated for 48 hours prior to extraction dramatically decreased from 30.2% to a trace value, whereas the concentration of the newly formed compounds achieved 23.6% of the dried extract (Table 2).

TABLE 2

| Experimental condition | Acetylated PFA concentration, % of dried extract | Acetyl free PFA concentration, % of dried extract |
|---|---|---|
| Fresh avocado seeds: immediate extraction after crushing | 30.2% | Less than 1% |
| Fresh avocado seeds: extraction begins 48 hours after crushing | 2.3% | 23.6% |
| Intact avocado seed stored for one month: immediate extraction after crushing | 28.4% | Less than 1% |

Physicochemical analysis of the newly formed compounds by GC/MS, $H^1$-NMR, and FTIR methods elucidated the structure of these compounds, which were identified as acetyl free (de-acetylated) PFA. This data was also confirmed by showing coincidence of gas chromatographic peaks of the newly formed compounds and the gas chromatographic peaks of the products of PFA alkaline hydrolysis.

No significant changes were observed in PFA type and level in intact avocado seeds that were stored at room temperature for 30 days before analysis. As shown in Table 2, the concentration of acetylated PFA in freshly separated seeds and in the intact seeds that were stored for one month at room temperature and atmospheric conditions were not practically different (Table 2), confirming that endogenous PFA de-acetylation is initiated by the crushing of the avocado seeds.

"incubating" in the context above means leaving crushed seeds alone, for a period allowing acetylated PFAs in the crushed avocado seeds to be endogenously de-acetylated. Such period is typically 10 minutes to approximately 48 hours.

Example 2

Endogenous De-Acetylation of PFA in Crushed Hass Avocado Seeds

The Ettinger avocados investigated in Example 1 are known to be very rich in oil content. Hass avocados, however, are more popular, and this example examines the PFA conversion in these avocados.

Avocado seeds were separated from Hass avocado pears and were crushed to bulk density ranges between 0.6-0.8 g/ml. 400 g samples of crushed seeds were introduced into sealed plastic bottles and were stored for 10 min, 8 hours and 48 hours at room temperature, followed by extraction with 600 milliliters of butyl acetate for 2 hours by intensive mixing of the samples with a stainless steel mixer. Extracts were filtered through Whatman filter paper #1 and butyl acetate was evaporated by rotor evaporation. Resulting dried extracts at 10 min and 48 h time points were analyzed by GC (Table 3a).

In addition, 2 g dried extracts were re-dissolved in 8 ml of hot hexane and then were placed in a cooling room having a temperature range between 5-8 C.° for 15-18 hours to allow cool crystallization. The crystallized product, consisting mainly of PFA, was separated from the solvent by filtration, and was quantified by GC analysis. PFA-depleted hexane extract was quantified for triglycerides the presence of other groups of extractive compounds was qualitatively determined.

Figure 2A:
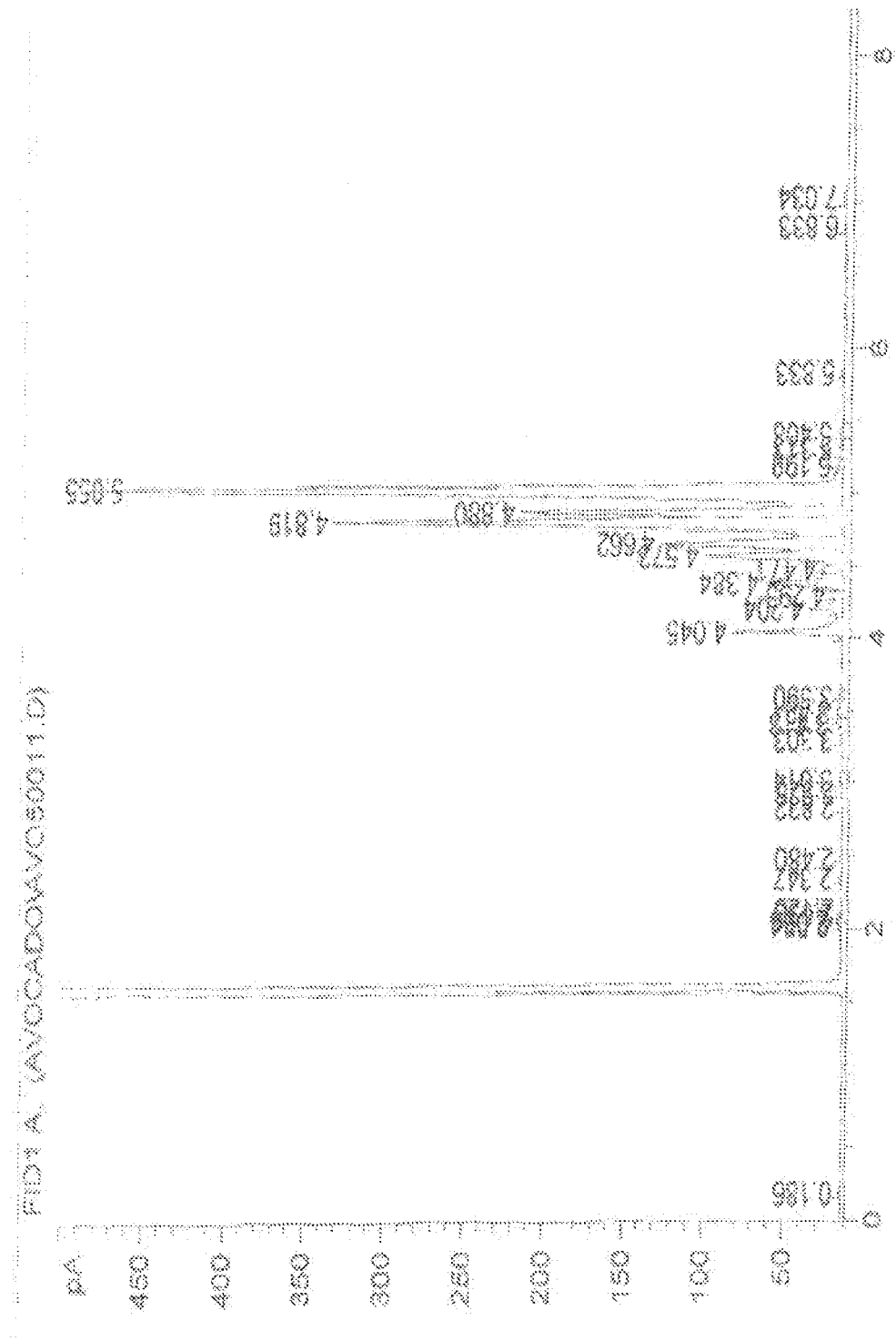
FIG. 2a shows a gas chromatograph of a samples obtained from extraction of raw undried crushed avocado seed, the extraction commencing 10 minutes after the crushing.
Figure 2B:
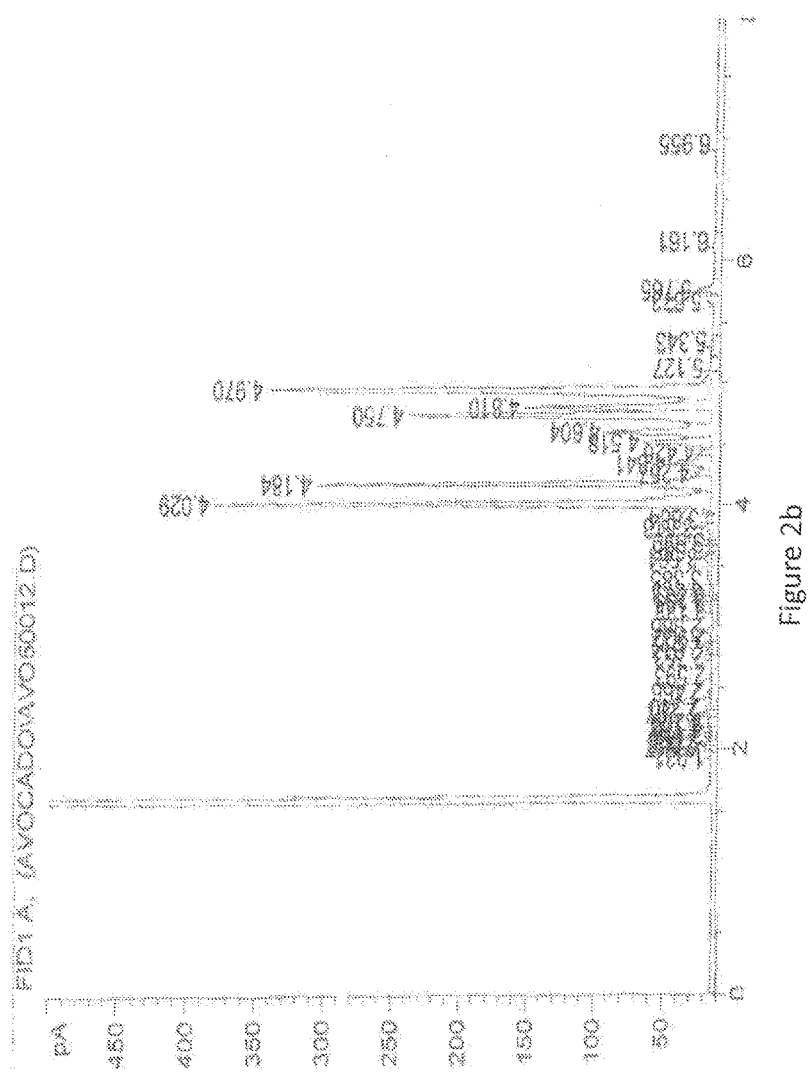
FIG. 2B shows the same but for extraction 8 hours after crushing.
Figure 2C:
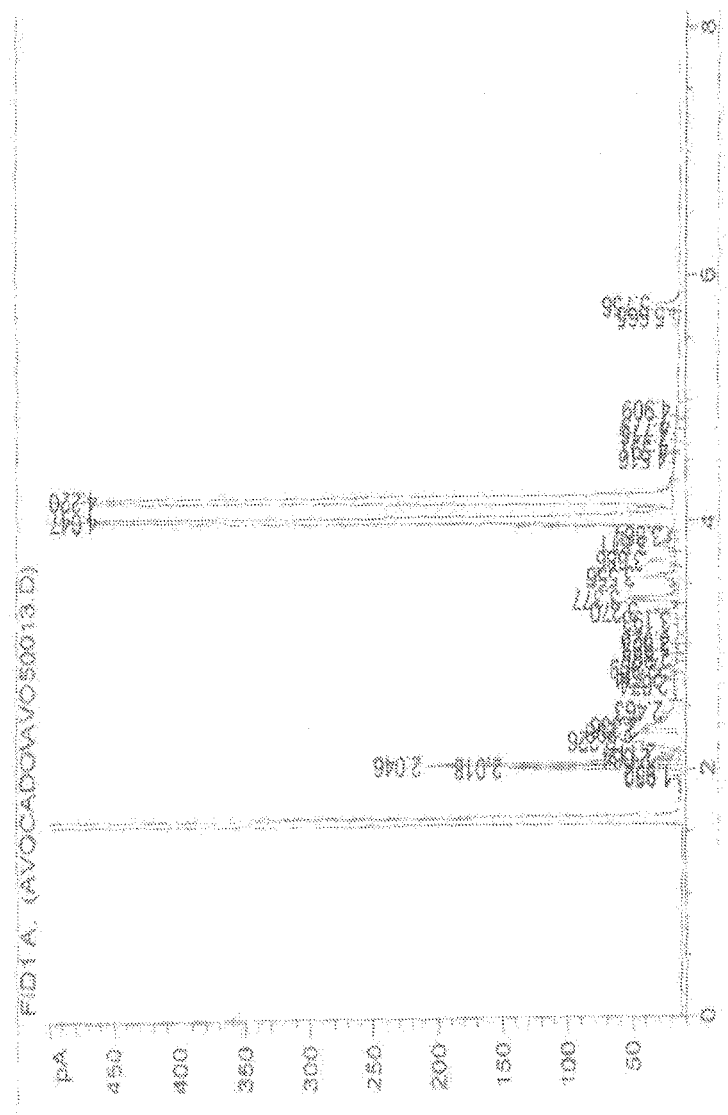
FIG. 2C shows the same for extraction 48 h after crushing.

Results:

Time dependent transformation of acetylated- to acetyl free PFA was visualized by GC-chromatography and is shown in FIGS. 2a-2c: GC-chromatography of crystalline PFA compounds isolated by cool precipitation from butyl acetate extracts (re-dissolved in hexane) of crushed Hass avocado seeds, FIG. 2a shows for extraction 10 minutes after crushing; FIG. 2B for extraction 8 hours after crushing; FIG. 2C shows for extraction 48 h after crushing.

Tables 3a and 3b summarize Transformation of acetylated PFA to acetyl free PFA in crushed Hass avocado seeds. Table 3a lists PFA concentration in butyl acetate extracts obtained 10 min and 48 hours after avocado grinding relative to the total extracts; Table 3b lists concentration of acetylated and acetyl free PFA in crystalline compounds isolated from butyl acetate extracts.

The concentration of acetylated fatty alcohols in the samples that were extracted 10 min after seed crushing was 23.8% of all extracted compounds. Acetyl free PFA was present at a minor concentration (2.9%) (Table 3a). In contrast, the concentration of acetyl free PFA apparently increased to 21.3% in the samples that were extracted 48 hours after seed crushing, whereas the concentration of the acetylated PFA was less than 1%. The content of total PFA in crystallized compounds isolated from the samples that were extracted 10 min, 8 hours and 48 hours after seed crushing were 93.7%, 83.6% and 73.5%, respectively. The concentration of acetyl free PFA in the isolated crystalline samples increased from 4.6% at 10 min time point to 48.0% at 8 hour time point and to 73.5% at 48 hours time point (Table 3b).

TABLE 3a

| Time after crushing | Concentration of acetylated PFA in butyl acetate extract, % | Concentration of acetyl free PFA in butyl acetate extract, % |
|---|---|---|
| 10 min | 23.8 | 2.9 |
| 48 hours | <1% | 21.3 |

TABLE 3b

| Time after crushing | Concentration of acetylated PFA, % | Concentration of acetyl free PFA ,% |
|---|---|---|
| 10 min | 89.1 | 4.6 |
| 8 hours | 35.6. | 48.0 |
| 48 hours | <1% | 73.0 |

Besides PFA, avocado seed extracts consist of up to 30% triglycerides. Other compounds present in the extract are typically furan lipids, pigments, sterols, vitamin E and unidentified hydrocarbons.

* Crushed avocado seeds were extracted for two hours with butyl acetate at 10 min, 8 h and 48 h after crushing. Butyl acetate was evaporated and extracts were re-dissolved in hot hexane followed by cool precipitation at 5° C.-8° C. for 15-18 h. Crystalline compounds were separated by filtration, washed with cool hexane, and analysed by GC.

The incubating is preferably for about 48 hours; "about" in the context of the present description generally being up to ±50% of the stated values, although specifically regarding the incubation period, in some embodiments the incubating is halted more early, particularly when a, mixture of acetylated and deacetylated PFAs is desired in which the amount of acetylated PFAs is larger than the amount of deacetylated PFAs.

Example 3

Endogenous De-Acetylation of PFA in Crushed Reed Avocado Seeds

This example demonstrates the same conversion phenomenon occurring in Reed avocados.

Avocado seeds were separated from Reed avocado pear and were crushed to bulk density ranges between 0.6-0.8 g/ml. 400 g samples of crushed seeds were introduced into covered plastic bottles and were stored for additional 10 min, 8 hour and 48 hours at room temperature and atmospheric conditions, followed by extraction with 600 milliliters of butyl acetate for 2 hours by intensive mixing of the samples by stainless steel mixer. Extracts were filtered through Whatman filter paper and the butyl acetate was evaporated by a rotor evaporator. Resulting dried extracts at 10 min and 48 h time points were analyzed by GC (Table 4).

Results.

The concentration of acetylated fatty alcohols in the samples that were extracted 10 min after seed crushing was about 30% of all extracted compounds. Acetyl free PFA was present at an average concentration of 5.9% as shown in Table 4, summarizing Transformation of acetylated PFA to acetyl free PFA in crushed Reed avocado seeds. In contrast, the concentration of acetyl free PFA was increased up to 24.5% in the samples that were extracted 48 hours after seed crushing, whereas the concentration of the acetylated PFA was less than 1%.

TABLE 4

| Experimental condition | Acetylated PFA concentration, % of dried extract | Acetyl free PFA concentration, % of dried extract |
|---|---|---|
| Fresh avocado seeds: extraction begins at 10 min after crushing | 30% | 5.9% |
| Fresh avocado seeds: extraction begins at 48 hour after crushing | <1% | 24.5% |

Any of the seed extracts prepared above. wherein the seeds were allowed to incubate to allow some acetylated PFAs to be deacetylated, are considered to have a substantial amount of deacetylated PFAs. In particular, a 10 minute incubation period suffices to allow a measurable conversion of the acetylated PFAs and thus the amount of deacetylated PFAs is substantial.

To summarize, the following are provided:

A process of obtaining avocado seed extracts containing essentially acetyl-free polyhydroxylated fatty alcohols is characterized, comprising a step of crushing avocado seeds following by incubation of grinded avocado seeds at atmospheric conditions until polyhydroxylated fatty alcohols are endogenously de-acetylated and then extracting crushed seeds in an organic solvent, preferably in butyl acetate.

Further provided is a process for obtaining avocado seed extracts containing both acetyl free and acetylated polyhydroxylated fatty alcohols in various ratios, characterized in that it comprises a step of crushing raw undried avocado seeds followed by incubating the raw undried crushed avocado seeds, until polyhydroxylated fatty alcohols in the crushed avocado seeds are endogenously de-acetylated to desired degree, and then in extracting crushed avocado seeds in an organic solvent, preferably in butyl acetate.

Further provided is a process for obtaining avocado seed extracts enriched with acetyl free and acetylated polyhydroxylated fatty alcohols, in various ratios, and with avocado seed triglycerides, characterized in that it comprises the step of grinding avocado seeds followed by incubating the crushed avocado until natural polyhydroxylated fatty alcohols are endogenously de-acetylated in the crushed avocado seeds to the desired degree, and then in extracting powdered avocado seed in an organic solvent, preferably in butyl acetate.

Yet further provided is a process for obtaining de-acetylated polyhydroxylated fatty alcohols or mixtures of de-acetylated and acetylated fatty alcohols or extracts enriched with de-acetylated polyhydroxylated fatty alcohols or with a mixture of acetylated and deacetylated fatty alcohols. The process is characterised in that dried avocado seed extracts obtained by the process described in paragraphs 1-3 are dissolved in hot hexane and polyhydroxylated fatty alcohols are separated by cool precipitation.

Cosmetic compositions for treating skin consisting active principle or extracts as obtained by the processes as described above may be prepared.

Pharmaceutical compositions comprising active principle or extracts as obtained by the processes described above are also provided.

For example, we are now in the process of CTFA registration of an extract containing up to 40% of PFAs. The extract is prepared for cosmetic application by the new technology, with optional enrichment of the final extract with crystalline PFA obtained by cool precipitation.

0.1% and 0.3% w/w cream preparations from the crystals formed by precipitation from hexane were tested for an ameliorative effect on 10 subjects after irritating their skin with SLS (Sodium Lauryl Sulfate), according to FDA procedure outlines and a satisfactory anti-inflammatory effect was observed in all subjects.

Typically, the extract content is: polyhydroxylated fatty alcohols—up to 40% of the extract; trigycerides—up to 30%; sterols—up to 5%; Others (including caratenoids and vitamin E)—up to 25%. Typically, the concentration of PFAs is 0.1-0.5% of the weight of the pharmaceutical delivery from or the cosmetics, such as a skin cream.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

The scope of the present invention is defined by the appended claims and includes both combinations and sub combinations of the various features described hereinabove as well as variations and modifications thereof, which would occur to persons skilled in the art upon reading the foregoing description.

The invention claimed is:

1. A process of obtaining avocado seed extracts comprising polyhydroxylated fatty alcohols (PFAs), the process comprising:
   crushing raw undried avocado seeds that were not subject to any type of drying treatment, to provide crushed avocado seeds at a bulk density between about 0.2 and 1.2 g/ml;
   incubating the crushed avocado seeds at a temperature between 15 and 45° C. for between 10 minutes to 48 hours; and
   extracting PFAs from the crushed seeds with an organic solvent selected from the group consisting of methanol and alkyl acetates or any combination thereof.

2. The process of claim 1, wherein the organic solvent is butyl acetate or ethyl acetate.

3. The process of claim 1, excluding alkaline saponification of the crushed seeds.

4. The process of claim 1, wherein about 1 to 6 parts of the solvent are used per about 1 part of the crushed seeds.

5. The process of claim 4, wherein about 3 parts of the solvent are used per about 2 parts of the crushed seeds.

6. The process of claim 1, the extracting comprising mixing the crushed seeds for about 1-5 hours with the solvent.

7. The process of claim 5, further comprising subsequently dissolving the extract in hot hexane at temperatures between 40-50° C.

8. The process of claim 7, further comprising cool precipitation of PFAs out of the hexane solution at a temperature between 4-8° C.

9. The process of claim 1, wherein after an incubation for at least an hour up to 15% of the total PFAs are deacetylated.

10. The process of claim 1, wherein after an incubation for 24 hours up to 40%-70% of the total PFAs are deacetylated.

11. The process of claim 1, wherein after an incubation for 48 hours all the PFAs are deacetylated.

* * * * *

UNITED STATES PATENT AND TRADEMARK OFFICE
CERTIFICATE OF CORRECTION

PATENT NO.           : 9,982,216 B2
APPLICATION NO.      : 14/414215
DATED                : May 29, 2018
INVENTOR(S)          : Joseph Segal et al.

Page 1 of 1

It is certified that error appears in the above-identified patent and that said Letters Patent is hereby corrected as shown below:

On the Title Page

Item (71) should be corrected to read:
Applicant: AVOMED LTD., Rosh Pina (IL)

Signed and Sealed this
Twenty-fifth Day of June, 2019

Andrei Iancu
*Director of the United States Patent and Trademark Office*